United States Patent
Cormier et al.

(10) Patent No.: US 10,385,995 B2
(45) Date of Patent: Aug. 20, 2019

(54) FLUIDIC COUPLING SEAL

(71) Applicant: Waters Technologies Corporation, Milford, MA (US)

(72) Inventors: Sylvain Cormier, Mendon, MA (US); Joshua A. Shreve, Franklin, MA (US); Joseph A. Luongo, Walpole, MA (US); Paul Keenan, Harrisville, RI (US); Kenneth Plant, Leominster, MA (US)

(73) Assignee: WATERS TECHNOLOGIES CORPORATION, Milford, MA (US)

(*) Notice: Subject to any disclaimer, the term of this patent is extended or adjusted under 35 U.S.C. 154(b) by 682 days.

(21) Appl. No.: 14/651,835

(22) PCT Filed: Dec. 16, 2013

(86) PCT No.: PCT/US2013/075383
§ 371 (c)(1),
(2) Date: Jun. 12, 2015

(87) PCT Pub. No.: WO2014/099777
PCT Pub. Date: Jun. 26, 2014

(65) Prior Publication Data
US 2015/0369403 A1     Dec. 24, 2015

Related U.S. Application Data

(60) Provisional application No. 61/739,798, filed on Dec. 20, 2012.

(51) Int. Cl.
| | | |
|---|---|---|
| *G01N 30/22* | (2006.01) | |
| *F16L 19/02* | (2006.01) | |
| *G01N 30/60* | (2006.01) | |

(52) U.S. Cl.
CPC ....... *F16L 19/0212* (2013.01); *F16L 19/0206* (2013.01); *G01N 30/6026* (2013.01); *G01N 30/22* (2013.01)

(58) Field of Classification Search
CPC .............. F16L 19/0212; F16L 19/0206; G01N 30/6026; G01N 30/22; G01N 30/6039
(Continued)

(56) References Cited

U.S. PATENT DOCUMENTS

| 3,326,583 A | * | 6/1967 | Guarnaschelli | ....... F16L 15/005 |
| | | | | 285/342 |
| RE27,709 E | * | 7/1973 | Holmgren | ........... F16L 19/0206 |
| | | | | 285/288 |

(Continued)

FOREIGN PATENT DOCUMENTS

| CN | 102439437 A | 5/2012 |
| DE | 10225960 C1 | 10/2003 |

(Continued)

OTHER PUBLICATIONS

Second Office Action in counterpart Chinese Patent Application No. 201380067225.2, dated Aug. 18, 2016; 18 pages.

(Continued)

*Primary Examiner* — Anna M Momper
*Assistant Examiner* — James A Linford
(74) *Attorney, Agent, or Firm* — Schmeiser, Olsen & Watts LLP

(57) ABSTRACT

Described is a coupling seal that includes a polymeric body having a bore extending from a first end to an internal sealing surface and a fluid channel extending from the internal sealing surface to a second end. The bore is configured to receive a tube having a fluid channel so that an endface of the tube engages the internal sealing surface. The second end of the polymeric body is configured to contact a sealing surface of a coupling body that has a fluid channel extending from the sealing surface. A fluidic seal occurs when the coupling seal is compressed between the endface and the sealing surface. A void between an outer surface of (Continued)

the polymeric body and an inner surface of the coupling body receives the deformation of the coupling seal while under compression to thereby prevent the fluid channel of the tube from being crushed or obstructed.

17 Claims, 6 Drawing Sheets

(58) Field of Classification Search
USPC .................................. 422/537, 538, 540, 544
See application file for complete search history.

(56) References Cited

U.S. PATENT DOCUMENTS

| | | | |
|---|---|---|---|
| 4,281,679 A * | 8/1981 | Stearns | F16K 15/04 137/515.5 |
| 4,529,230 A * | 7/1985 | Fatula, Jr. | G01N 30/6039 285/341 |
| 4,619,473 A | 10/1986 | Someya | |
| 5,595,406 A | 1/1997 | Warchol | |
| 6,209,928 B1 | 4/2001 | Benett et al. | |
| 6,273,478 B1 | 8/2001 | Benett et al. | |
| 2012/0061955 A1 | 3/2012 | Hochgraeber et al. | |
| 2014/0119696 A1 | 5/2014 | Lin | |

FOREIGN PATENT DOCUMENTS

| | | | |
|---|---|---|---|
| DE | 10 2010 031663 A1 | 1/2012 | |
| JP | 08304370 A * | 11/1996 | ......... G01N 30/6026 |
| WO | 9963260 A1 | 12/1999 | |
| WO | 2010/000324 A1 | 1/2010 | |
| WO | 2012118996 A1 | 9/2012 | |
| WO | 2012177403 | 12/2012 | |
| WO | 2013174421 | 11/2013 | |

OTHER PUBLICATIONS

International Preliminary Report on Patentability in counterpart International Patent Application No. PCT/US13/75383, dated Jul. 2, 2015; 6 pages.
Extended Search Report in counterpart European Patent Application No. 13864021.4, dated Sep. 13, 2016; 9 pages.
"DuPont(TM) Vespel(R) SCP-5009 HPLC Rotor Seal in Analytical Instrumentation," DuPont.com, Apr. 2011; 2 pages.
Third Office Action in counterpart Chinese Patent Application No. 201380067225.2, dated Feb. 8, 2017; 17 pages.
International Search Report and Written Opinion in International Patent Application No. PCT/US2013/075383, dated Apr. 30, 2014; 7 pages.
First Office Action in related Chinese patent application No. 201380067225.2 dated Dec. 23, 2015; 20 pages.
European Search Report in counterpart European Patent Application No. 13864021.4, dated Apr. 18, 2018; 6 pages.
Examination Report in European Patent Application No. 13864021.4, dated Apr. 26, 2017; 5 pages.

* cited by examiner

FLUIDIC COUPLING SEAL

RELATED APPLICATIONS

This application claims the benefit of and priority to U.S. provisional application No. 61/739,798, filed Dec. 20, 2012, entitled "FLUIDIC COUPLING SEAL," the entirety of which is incorporated by reference herein.

FIELD OF THE INVENTION

The invention relates generally to fluidic couplings. More particularly, the invention relates to a coupling seal for a high pressure fluidic coupling.

BACKGROUND

Chemical analysis systems often include fluid channels that accommodate high pressures. For example, a liquid chromatography system, such as a system designed for ultra performance liquid chromatography (UPLC), can operate at pressure that may exceed 18,000 psi. The fluid channels in such systems may include tubing that is coupled to other components or tubing using a conventional coupling such as a standard compression fitting.

The improved performance of UPLC systems includes substantial increases in separation power. Adverse chromatographic effects such as carryover and peak tailing can result from the use of conventional couplings used to achieve fluid-tight seals and are more readily observable in system measurements. In typical couplings, the seal is formed along the side of the capillary. For example, many couplings use an annular sealing element such as a ferrule that has a conical outer surface. To form a fluid-tight coupling, a capillary having the annular sealing element displaced away from the endface is inserted into a receptacle of a coupling body. The receptacle is defined by a cylindrical bore that transitions to a conical bore which transitions to a smaller diameter cylindrical bore. A fluid channel extends from the surface at the bottom of the smaller diameter cylindrical bore into the coupling body. The cone angle of the conical bore is greater than the cone angle of the annular sealing element resulting in a seal along the circumferential contact between the annular sealing element and the conical surface of the conical bore. Additional force applied by a compression screw after achieving initial contact between the annular sealing element and conical bore surface results in a contact seal between the annular sealing element and the outer surface of the capillary. If the endface of the capillary is not in contact with the bottom of the cylindrical bore, the region between the outer surface of the capillary and the side wall of the smaller cylindrical bore below the circumferential contact seal represents an unswept volume. During a chromatographic measurement, analytes can become trapped in the unswept volume and gradually diffuse into the fluid flow, thereby degrading the chromatographic measurement data. Moreover, corrosion may occur at the capillary interface, leading to further degradation of chromatographic measurements.

SUMMARY

In one aspect, the invention features a coupling seal such as that used with a fluidic coupling for a capillary. The coupling seal includes a polymeric body having a first end, a second end opposite to the first end, a first outer surface extending from the first end and having a cylindrical shape, and a second outer surface extending from the first outer surface to the second end. The polymeric body has a bore extending from the first end to an internal sealing surface and also has a fluid channel extending from the internal sealing surface to the second end. The bore is configured to receive a tube having a fluid channel so that an endface of the tube engages the internal sealing surface. The second end of the polymeric body is configured to engage a sealing surface of a coupling body having a fluid channel extending from the sealing surface. The second outer surface of the polymeric body and an internal surface of the coupling body define a deformation volume to receive a deformation of the polymeric body when under compression. A fluidic seal is formed between the fluid channel of the tube and the fluid channel of the coupling body when the polymeric body is under compression.

In another aspect, the invention features a fluidic coupling such as that used to couple a fluid path of a capillary to another fluid path. The fluidic coupling includes a tube, a coupling body and a coupling seal. The tube has a fluid channel and an endface. The coupling body has an outer surface, an internal sealing surface, at least one bore and a fluid channel extending into the coupling body from the internal sealing surface. The at least one bore extends from the outer surface to the internal sealing surface. The coupling seal includes a polymeric body having a first end, a second end opposite to the first end, a first outer surface extending from the first end and having a cylindrical shape, and a second outer surface extending from the first outer surface to the second end. The polymeric body has a bore that extends from the first end to an internal sealing surface. The polymeric body also has a fluid channel extending from the internal sealing surface to the second end. A portion of the tube is disposed in the bore of the polymeric body so that the endface is in contact with the internal sealing surface. The polymeric body is disposed in the bore of the coupling body so that the second end is in contact with the internal sealing surface of the coupling body. The second outer surface of the polymeric body and an internal surface of the coupling body define a deformation volume to receive a deformation of the polymeric body when the polymeric body is under compression. A fluidic seal is formed between the fluid channel of the tube and the fluid channel of the coupling body when the polymeric body is under compression.

BRIEF DESCRIPTION OF THE DRAWINGS

The above and further advantages of this invention may be better understood by referring to the following description in conjunction with the accompanying drawings, in which like reference numerals indicate like elements and features in the various figures. For clarity, not every element may be labeled in every figure. The drawings are not necessarily to scale, emphasis instead being placed upon illustrating the principles of the invention.

DETAILED DESCRIPTION

Figure 1:
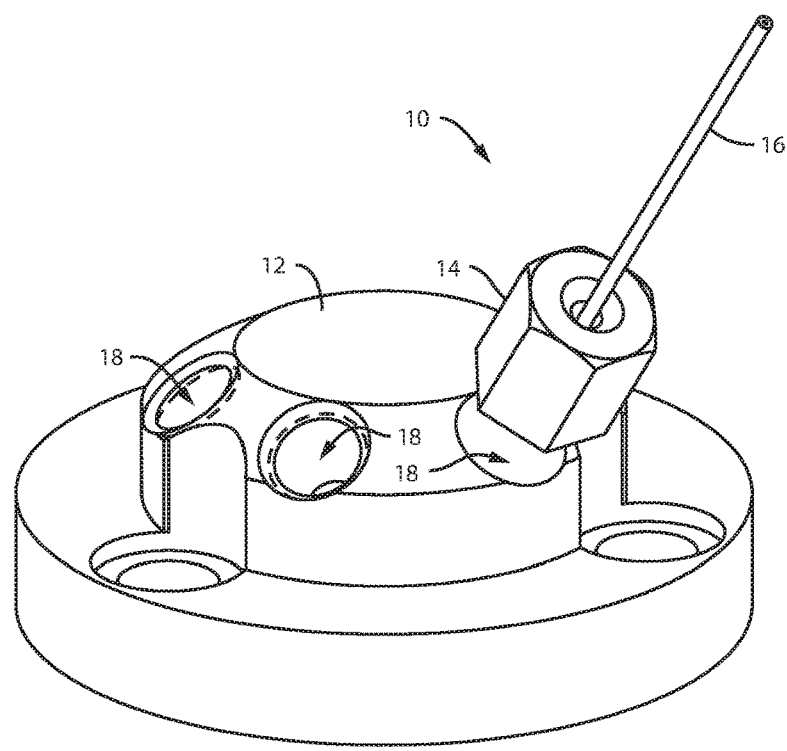
FIG. 1 is an illustration of a capillary coupling at a stator portion of a rotary shear seal valve for a liquid chromatography system.

Reference in the specification to "one embodiment" or "an embodiment" means that a particular, feature, structure or characteristic described in connection with the embodiment is included in at least one embodiment of the teaching. References to a particular embodiment within the specification do not necessarily all refer to the same embodiment.

The present teaching will now be described in more detail with reference to exemplary embodiments thereof as shown in the accompanying drawings. While the present teaching is described in conjunction with various embodiments and examples, it is not intended that the present teaching be limited to such embodiments. On the contrary, the present teaching encompasses various alternatives, modifications and equivalents, as will be appreciated by those of skill in the art. Those of ordinary skill having access to the teaching herein will recognize additional implementations, modifications and embodiments, as well as other fields of use, which are within the scope of the present disclosure as described herein.

In brief overview, the invention relates to a coupling seal that can be used, for example, in a fluidic coupling for a capillary. The coupling seal includes a polymeric body that has a bore extending from a first end to an internal sealing surface and a fluid channel extending from the internal sealing surface to a second end. The bore is configured to receive a tube having a fluid channel so that an endface of the tube engages the internal sealing surface. The second end of the polymeric body is configured to contact a sealing surface of a coupling body that has a fluid channel extending from the sealing surface. A fluidic seal is achieved when the coupling seal is compressed between the endface of the tube and the sealing surface of the coupling body. A void between an outer surface of the polymeric body and an inner surface of the coupling body acts as a deformation volume that accepts the deformation of the coupling seal while under compression to thereby prevent the fluid channel of the tube from being crushed or obstructed.

Although other forms of couplings are available to reduce carryover and dispersion, such couplings do not have the ease of use associated with couplings utilizing the coupling seal of the present invention. Moreover, these other forms of couplings are generally more expensive to use if a leak develops at the coupling because the complete capillary assembly has to be replaced and the end of the capillary can be obstructed if the coupling is over tightened.

As used herein, a coupling body means a body that has a bore to receive a tube assembly and a fluid channel to receive a fluid from or provide a fluid to the tube assembly. For example, a coupling body can be a structure provided between the endfaces of two capillaries (or tube assemblies) to enable fluid to pass from one capillary to the other capillary. Alternatively, a system component can include a coupling body. By way of examples, an injector valve or column for a liquid chromatography system may include a coupling body to couple fluid to or from a capillary or another component of a liquid chromatography system.

As used herein, the words "tube" and "capillary" are used interchangeably. A "tube assembly" refers to a tube or capillary that includes additional structure such as a sleeve or outer tube attached or otherwise secured to the tube or capillary.

FIG. 1 shows a view of a capillary coupling 10 at a stator portion 12 of a rotary shear seal valve for a liquid chromatography system. The fluidic coupling 10 includes a compression nut 14 and additional components (not visible). A tube 16 defines a fluid channel that conducts a fluid from a chromatographic system component to one of the stator ports 18 or from the stator port 18 to the chromatographic system component. By way of examples, the chromatographic system component can be an injection valve or a chromatography column A second fluid channel is defined inside the stator portion 12 and interfaces with a rotor portion of the rotary shear seal valve to couple, or decouple, the second fluid channel with a third fluid channel in communication with one of the other stator ports 18.

Figure 2B:
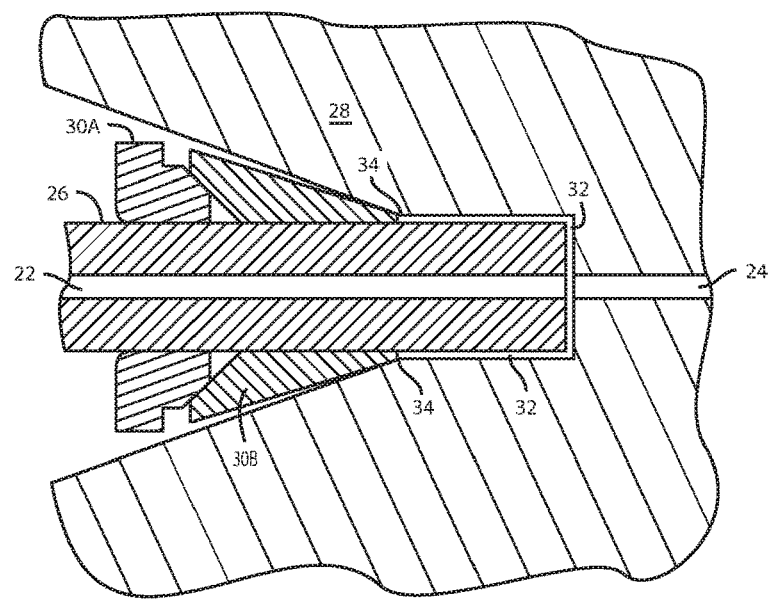
FIG. 2B is an expanded cross-sectional view of a portion of the conventional fitting of FIG. 2A showing the sealing interface.
Figure 2A:
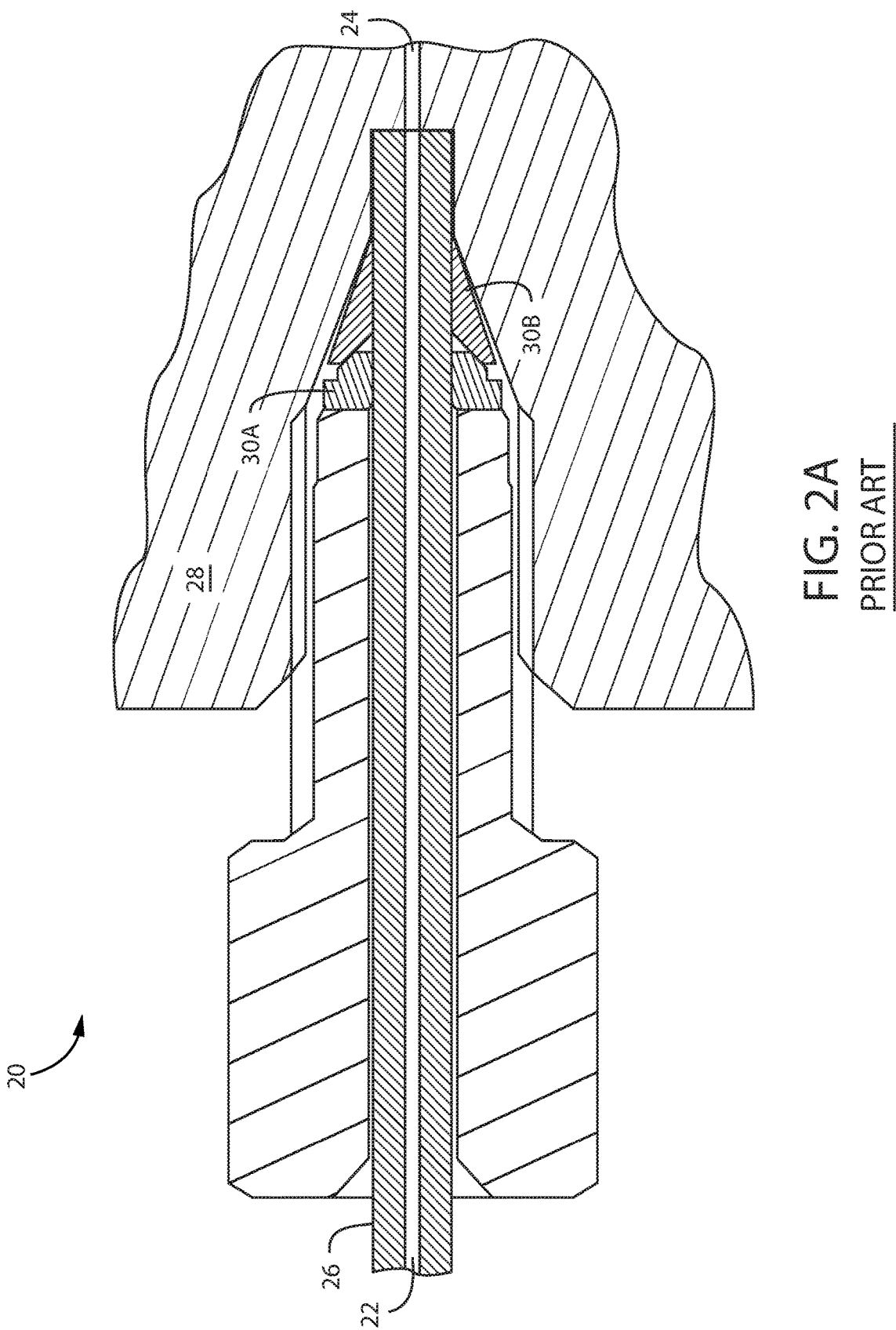
FIG. 2A is a cross-sectional view of a conventional fitting used to couple two fluid channels to each other.

FIG. 2A shows a cross-sectional view of a conventional fitting 20 that can be used, for example, to couple two fluid channels 22 and 24. For example, the fitting 20 can be used to couple the tube 16 of FIG. 1 to an internal fluid channel in the rotary shear seal valve. The tube 26 includes the first fluid channel 22 which is coupled to the second fluid channel 24 inside the coupling body 28. FIG. 2B is an expanded view of a portion of FIG. 2A that shows the sealing interface. A two-part ferrule 30A and 30B engages an inner conical surface of the coupling body 28 and the outer surface of the tube 26. The resulting fluidic seal can withstand a high fluid pressure (e.g., greater than 15,000 psi); however, an unswept volume 32 is formed in the unoccupied region of the bore that surrounds the tube 26 and is to the right of the contact zone 34 (i.e., where the ferrule part 30B is in contact with the conical surface) in the figure. The presence of the unswept volume 32 may result in sample carryover. For example, as the sample moves from the first fluid channel 22 into the second fluid channel 24, some of the sample can diffuse into the unswept volume 32. Subsequently, the sample present in the unswept volume 32 can diffuse back into the main fluid flow and into the second fluid channel 24. If the fitting 20 is used with components of a liquid chromatography system, such as illustrated in FIG. 1, the fluid sample that diffuses back into the fluid flow (i.e., the carryover) can adversely affect chromatographic measurements.

Figure 3A:
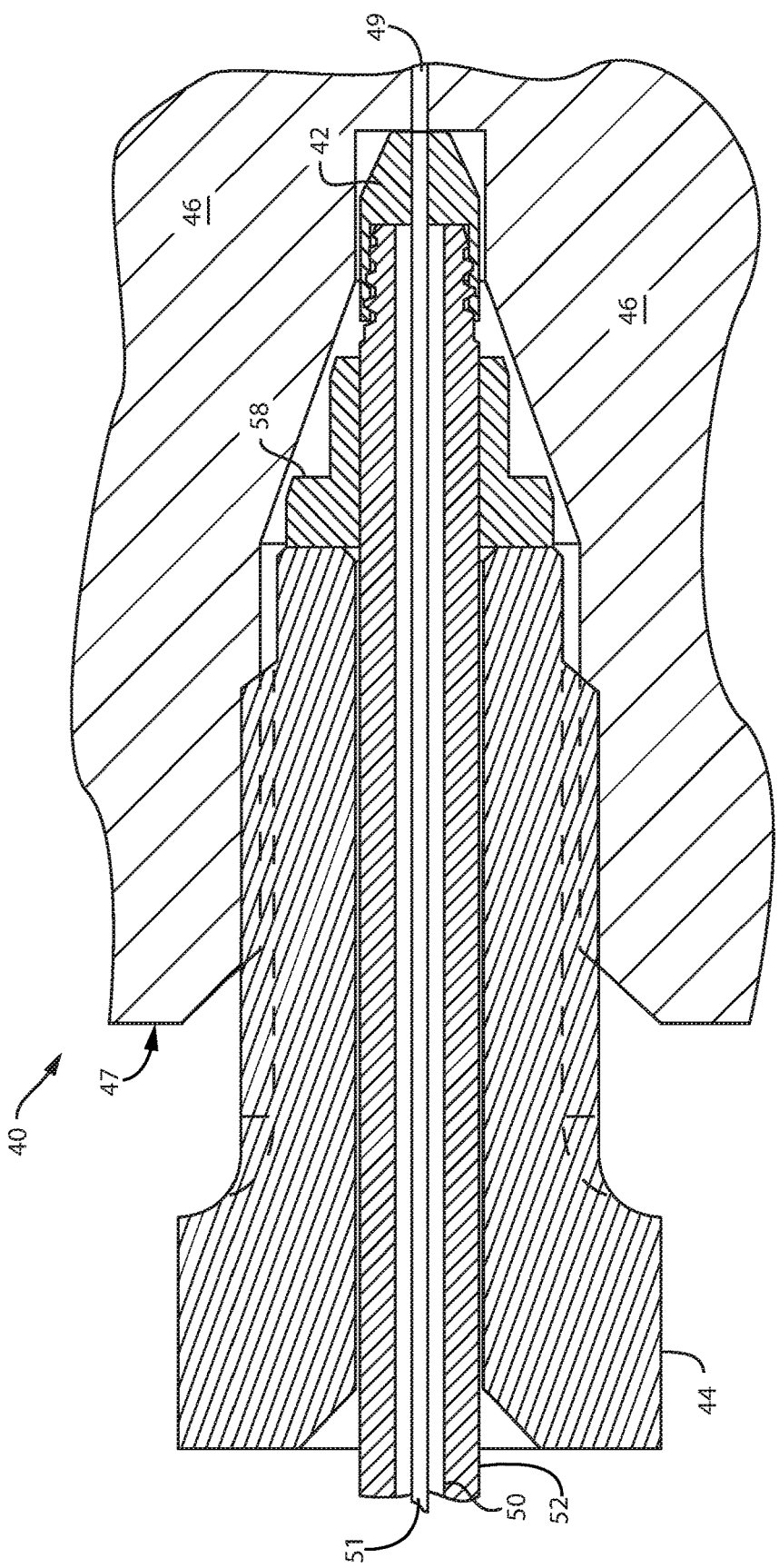
FIG. 3A is a cross-sectional view of an embodiment of a fluidic coupling according to the invention.
Figure 3B:
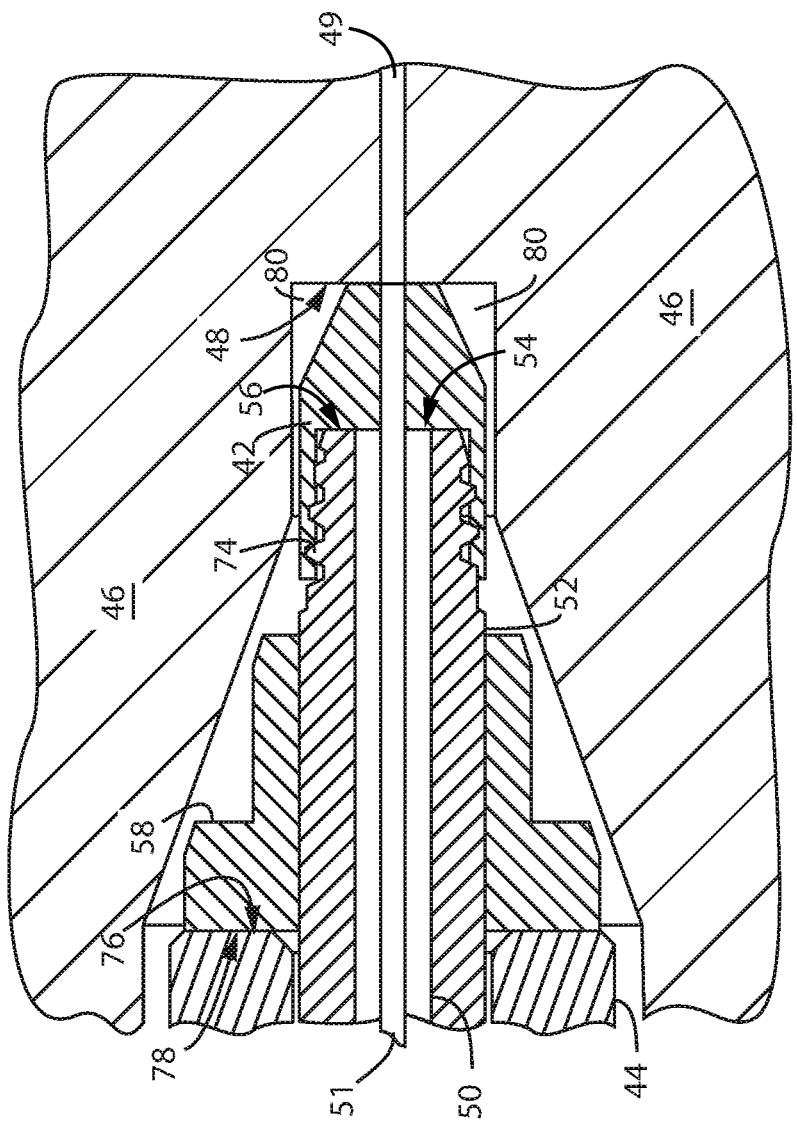
FIG. 3B is an expanded cross-sectional view of the fluidic coupling of FIG. 3A showing an uncompressed coupling seal.

FIG. 3A is a cross-sectional view of an embodiment of a fluidic coupling 40 in accordance with principles of the invention. FIG. 3B is an expanded cross-sectional view of the fluidic coupling 40 in the region of a coupling seal 42. The fluidic coupling 40 includes the coupling seal 42, a tube assembly, a compression screw 44 and a coupling body 46. The coupling body 46 has a receptacle that includes a first bore extending from an external surface 47, a second bore having a smaller diameter than the first bore, and a conical cavity between the first and second bores. A first fluid channel 49 extends from an internal sealing surface 48 at the end of the second bore opposite the conical cavity and through the coupling body 46. The tube assembly includes a stainless steel capillary 50 that defines a second fluid channel 51. The capillary 50 is encircled along a portion of its length at one end by a tube sleeve 52. In one embodiment, the inner diameter of the capillary 50 is 0.007 in. and the outer diameter of the tube sleeve 52 is 0.026 in. The capillary 50 and tube sleeve 52 are joined to each other, for example, by a face-weld so that their endfaces 54 and 56, respectively, are substantially coplanar. The weld can be a laser weld or an electron beam weld as are known in the art. A ferrule 58 encircles the tube sleeve 52. In some embodiments, the capillary 50, tube sleeve 52 and ferrule 58 are stainless steel. A portion of the outer surface of the tube sleeve 52 that extends between the ferrule 58 and endface 54 is tapered to allow for easy insertion into the coupling seal 42 as described below. Optionally, at least a portion of the tapered outer surface includes threads 74 to assist in securing the coupling seal 42 to the tube assembly.

The coupling seal 42 is fabricated from a body formed of a polymer such as a polyimide-based plastic (e.g., Vesper available from Dupont® of Wilmington, Del.) or other high strength polyimide. As shown in the cross-sectional view of FIG. 4, the coupling seal 42 has a cylindrical outer surface 60 that extends a length $L_1$ from a first end 62 and then transitions to a chamfer 64 that extends a length $L_2$ to a second end 66 that is opposite to the first end 62. A bore 68 having a depth D extends from the first end 62 to an internal sealing surface 70. A fluid channel 72 extends from the internal sealing surface 70 to the second end 66. Preferably, the outer diameter of the coupling seal 42 is approximately the same as the outer diameter of the tube sleeve 52. In one embodiment, the diameter of the fluid channel 72 is 0.008 in and the diameter of the cylindrical outer surface 60 is 0.062 in.

Referring also back to FIGS. 3A and 3B, to assemble the fluidic coupling 40, the coupling seal 42 is urged onto the end of the tube assembly until the internal sealing surface 70 is in contact with the endfaces 54 and 56. When the tube assembly is fully inserted, the coupling seal 42 flares outward near its first end 62 due to the larger diameter end of the tapered outer surface of the tube sleeve 52. The combined tube assembly, ferrule 58 and coupling seal 42 are inserted into the receptacle. Threads on the compression screw 44 engage threads along the inner surface of the first bore in the coupling body 46. As the compression screw 44 is rotated, the screw thrust surface 76 engages a back surface 78 of the ferrule 58. Continued rotation of the compression screw 44 results in moving the ferrule 58 and tube assembly further into the receptacle until the second end 66 of the coupling seal 42 comes into contact with the internal sealing surface 48 of the coupling body 46. Further rotation results in axial compression of the coupling seal 42 while the endfaces 54 and 56 remain in contact with the internal sealing surface 70 of the coupling seal 42 and the second end 66 of the coupling seal 42 remains in contact with the internal sealing surface 48 at the end of the second bore in the coupling body 46. Advantageously, the polymeric material composition allows the coupling seal 42 to deform and flow into the unoccupied volume (i.e., "deformation volume") of the second bore without crushing or otherwise compressing the capillary 50. In the embodiment shown in FIG. 4, the deformation volume 80 is (represented by the two triangular regions in the figure) is the difference of two volumes: a first volume defined by the coupling seal 42 over the length $L_2$ if it were to have a cylindrical outer surface of the same diameter as the cylindrical outer surface along $L_1$ and a second volume defined by the actual volume of the coupling seal 42 along the length $L_2$.

Figure 3C:
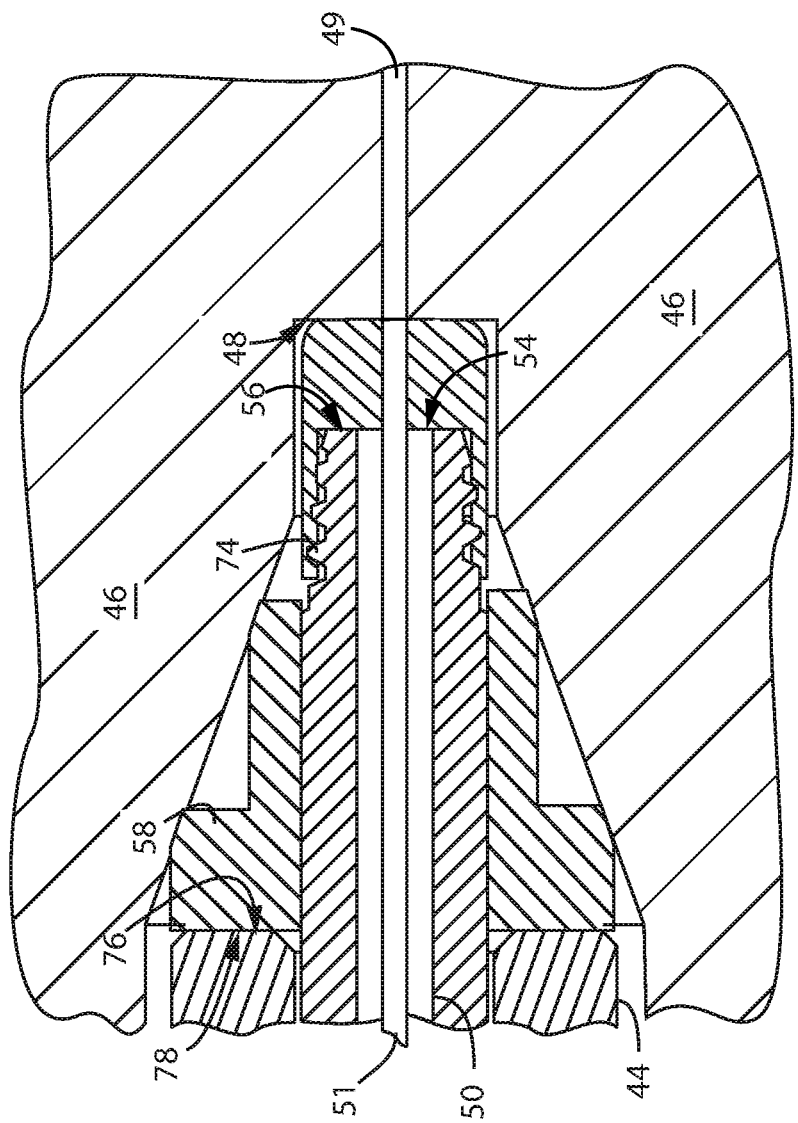
FIG. 3C shows the fluidic coupling of FIG. 3B with the coupling seal under compression.

Referring to FIG. 3C, continued rotation of the compression screw 44 results in pushing the tube assembly further into the receptacle until the ferrule 58 contacts the inner surface of the coupling body 46 surrounding the conical cavity. The coupling seal 42 is deformed such that a portion of the polymeric body flows or deforms into a portion of the deformation volume 80 (see FIG. 4). The ferrule 58 thus provides a means to limit the insertion depth of the tube assembly into the receptacle. Limiting the insertion depth prevents the coupling seal 42 from deforming sufficiently to fill the deformation volume 80. Otherwise, once the coupling seal 42 deforms to consume the entire deformation volume, continue rotation of the compression screw 44 would result in radial compression of the fluid channel 72 until eventually the fluid channel 72 would collapse.

Advantageously, the selection of appropriate dimensions for the receptacle, coupling seal 42 and ferrule 58 enable radial compression imparted by the coupling seal 42 to the tube assembly to be avoided. Due to the allowable range of compression and deformation of the coupling seal 42, machining and fabrication tolerances are not stringent and are easily satisfied using standard practices.

The seal occurs at the endface of the capillary 50 therefore an unswept volume and its associated problems of carryover and peak tailing are avoided. Moreover, corrosion that may otherwise occur at capillary interfaces due to fluid within an unswept volume is substantially reduce or eliminated. The coupling seal 42 can be used repeatedly in the same coupling body 46 and can easily be changed if the tube assembly needs to be coupled with a different coupling body. The coupling seal 42 is secured on the tube assembly due to friction. The coupling seal 42 can be accessed once the tube assembly is removed from the coupling body 46 and may easily be removed from the tube assembly by hand.

Figure 4:
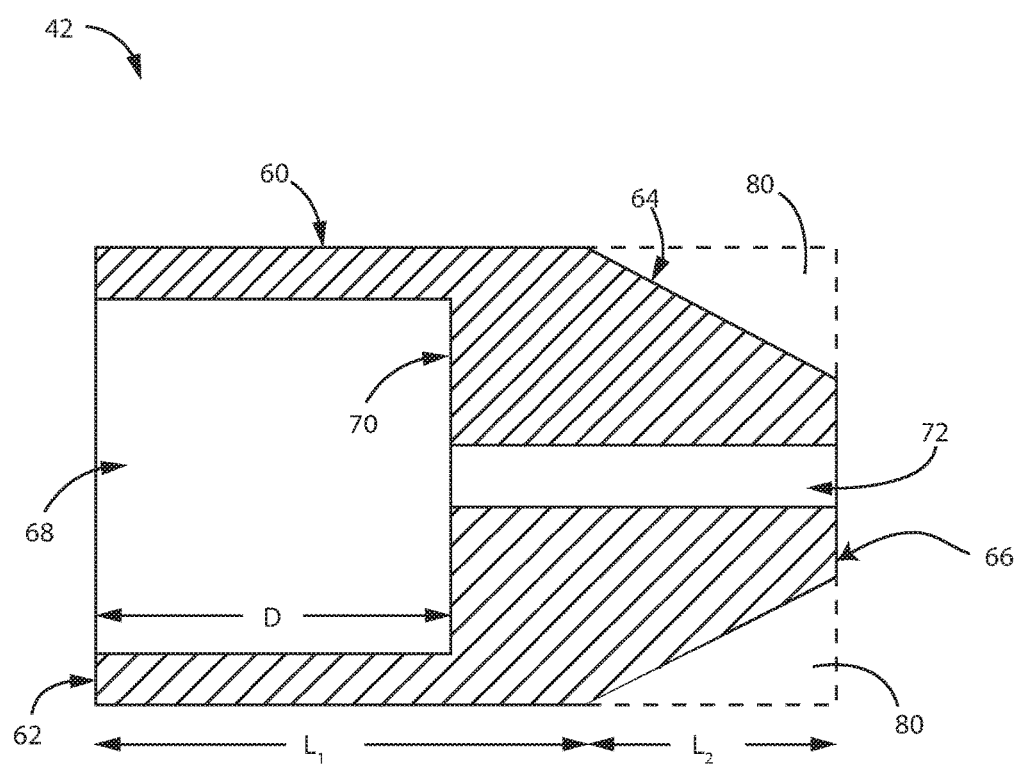
FIG. 4 is a cross-sectional view of the coupling seal of FIG. 3B.

In the embodiment shown in FIG. 4, the coupling seal 42 includes a cylindrical outer surface 60 that extends a length $L_1$ from the first end 62 and a chamfer 64 that extends a length $L_2$ from the cylindrical outer surface 60 to the second end 66. The chamfer 64 in part defines the available deformation volume 80 to accept the deformation of the coupling seal 42 when under axial compression. In alternative embodiments, the chamfer 64 is replaced by a different outer surface shape to define a deformation volume in the coupling body 42 sufficient to accommodate the deformation flow of the coupling seal 42 over the range of possible insertion depths. For example, the diameter of the outer shape is not required to monotonically decrease along the length $L_2$. In addition, the outer surface along the length $L_2$ is not required to be rotationally symmetric. In general, any shape of the outer surface along the length $L_2$ can be used as long as the resulting deformation volume is sufficient to receive the deformation of the coupling seal 42 when the tube assembly is fully inserted.

In some embodiments, the ferrule 58 is replaced by a different form of thrust sleeve such as a collet secured to the outer surface of the tube sleeve. The collet has a first surface to receive the screw thrust surface 76 of the compression screw 44. In other embodiments, the bore in the coupling body 46 can have different shapes. In one embodiment, the conical cavity is absent. Instead, a second surface on the collet is used to engage a surface defined by the step change in the diameters of the bores in the coupling body 46, thereby acting as a stop to limit the insertion depth of the tube assembly. In another embodiment, the ferrule 58 and tube 52 are machined as a single part.

While the invention has been shown and described with reference to specific embodiments, it should be understood by those skilled in the art that various changes in form and detail may be made therein without departing from the spirit and scope of the invention as recited in the accompanying claims.

The claims are as follows:

1. A coupling seal comprising:
    a polymeric body having a first end, a second end opposite to the first end, a first outer surface extending from the first end and having a cylindrical shape, and a chamfered second outer surface extending from the first outer surface to the second end, the polymeric body having a bore extending from the first end to a polymeric body internal sealing surface and having a fluid channel extending from the polymeric body internal sealing surface to the second end, the bore configured to receive a tube having a fluid channel so that an endface of the tube engages the polymeric body internal sealing surface, the second end of the polymeric body engages a coupling body internal sealing surface of a coupling body and deform and flow into an unoccupied volume when subject to compression against the coupling body internal sealing surface such that a fluidic seal is formed between the second end of the polymeric body and the coupling body internal surface when the polymeric body is under compression.

2. The coupling seal of claim 1, wherein the second end of the polymeric body is a flat surface having an opening defined by the fluid channel.

3. The coupling seal of claim 1 wherein the polymeric body is formed of a polyimide.

4. The coupling seal of claim 1, further comprising:
   a tube having a fluid channel and an endface;
   a tube sleeve disposed on the tube adjacent to the endface; and
   a thrust sleeve secured to an outer surface of the tube sleeve and having a surface configured to receive a thrust surface of a compression screw and thereby subject the polymeric body to compression against the coupling body internal sealing surface.

5. The coupling seal of claim 4, wherein the thrust sleeve includes a second surface that is configured to contact an inner surface of a conical cavity of the coupling body when the polymeric body is under compression.

6. The coupling seal of claim 5, wherein the thrust sleeve is configured to limit insertion of the tube sleeve and the tube into the second bore of the coupling body by the second surface contacting the conical cavity.

7. A fluidic coupling comprising:
   a tube having a fluid channel and an endface;
   a coupling body having an outer surface, a coupling body internal sealing surface, a first bore extending from an external surface, a second bore having a smaller diameter than the first bore extending from the coupling body internal sealing surface, a conical cavity between the first and second bores, and a fluid channel extending into the coupling body from the coupling body internal sealing surface, the first bore, the second bore, and the conical cavity extending from the outer surface to the coupling body internal sealing surface; and
   a coupling seal comprising a polymeric body having a first end, a second end opposite to the first end, a first outer surface extending from the first end and having a cylindrical shape, and a chamfered second outer surface extending from the first outer surface to the second end, the polymeric body having a bore extending from the first end to a polymeric body internal sealing surface and having a fluid channel extending from the polymeric body internal sealing surface to the second end, a portion of the tube being disposed in the bore of the polymeric body so that the endface is in contact with the polymeric body internal sealing surface, the polymeric body disposed in the bore of the coupling body so that the second end is in contact with the coupling body internal sealing surface, the chamfered second outer surface of the polymeric body and an internal surface of the coupling body defining a deformation volume to receive a deformation of the polymeric body when under axial compression, wherein a fluidic seal is formed between the fluid channel of the tube and the fluid channel of the coupling body when the polymeric body is under compression.

8. The fluidic coupling of claim 7 further comprising:
   a tube sleeve disposed on the tube adjacent to the endface; and
   a thrust sleeve secured to an outer surface of the tube sleeve and having a surface configured to receive a thrust surface of a compression screw and thereby urge the tube sleeve and tube into the at least one bore of the coupling body.

9. The fluidic coupling of claim 8 wherein the thrust sleeve is a ferrule.

10. The fluidic coupling of claim 8 wherein the thrust sleeve is a collet.

11. The fluidic coupling of claim 8 wherein the first bore of the coupling body has a threaded surface, the fluidic coupling further comprising a compression screw in engagement with the threaded surface and having a thrust surface to engage the surface of the thrust sleeve.

12. The fluidic coupling of claim 8 wherein a diameter of the second bore of the coupling body is greater than a diameter of the first outer surface of the polymeric body.

13. The fluidic coupling of claim 8 wherein an outer surface of the tube sleeve is tapered at an end proximate to the endface of the tube.

14. The fluidic coupling of claim 8, wherein a second surface of the thrust sleeve contacts an inner surface of the conical cavity when the polymeric body is under compression.

15. The fluidic coupling of claim 14, wherein contact between the second surface and the conical cavity is configured to limit insertion of the tube sleeve and the tube into the second bore of the coupling body.

16. The fluidic coupling of claim 15, wherein the first outer surface of the polymeric body is adjacent to the second bore of the coupling body when the polymeric body is under compression.

17. The fluidic coupling of claim 7, wherein the second end of the polymeric body is a flat surface having an opening defined by the fluid channel.

* * * * *